United States Patent [19]
Diep et al.

[11] Patent Number: 6,007,997
[45] Date of Patent: Dec. 28, 1999

[54] HUMAN CYSTEINE PROTEASE

[75] Inventors: Dinh Diep, San Francisco; Scott Michael Braxton, San Mateo; Angelo M. Delegeane, Hayward, all of Calif.

[73] Assignee: Incyte Pharmaceuticals, Inc., Palo Alto, Calif.

[21] Appl. No.: 09/193,524

[22] Filed: Nov. 17, 1998

Related U.S. Application Data

[62] Division of application No. 08/928,613, Sep. 12, 1997, Pat. No. 5,840,562.

[51] Int. Cl.$^6$ .............................. C12Q 1/68; L07H 21/04; C12N 15/85
[52] U.S. Cl. ............................ 435/6; 536/23.1; 536/24.5; 435/325
[58] Field of Search ................................ 536/23.1, 24.31, 536/24.5; 514/44; 435/6, 91.1, 325, 366, 377

[56] References Cited

PUBLICATIONS

Rojanasakul et al., Antisense oligonucleotidde therapeutics: drug delivery and targeting, Advanced Drug Delivery Reviews, vol. 18, pp. 115–131, 1996.

Gewirtz et al., Facilitating oligonucleotide delivery: helping antisense deliver on its promise, Proc. Natl. Acad. Sci., vol. 93, pp. 3161–3163, Apr. 1996.

Branch, A good antisense molecule is hard to find, TIBS, vol. 23, pp. 45–50, Feb. 1998.

Bouillaud, F., (Direct Submission), GenBank Sequence Database (Accession R17110), National Center for Biotechnology Information, National Library of Medicine, Bethesda, Maryland, 20894 (GI 770720), Jul. 11, 1995.

Okubo, K., et al., (Direct Submission), GenBank Sequence Database (Accession No. D12242), National Center for Biotechnology Information, National Library of Medicine, Bethesda, Maryland, 20894 (GI 767729), Nov. 18, 1992.

Hillier, L., (Direct Submission), GenBank Sequence Database (Accession R66824), National Center for Biotechnology Information, National Library of Medicine, Bethesda, Maryland, 20894 (GI 839462), Apr. 19, 1995.

Merckelbach, A. et al., "cDNA sequences of *Schistosoma japonicum* coding for two cathepsin B–like proteins and Sj32", *Trop. Med. Parasitol.*, 45: 193–198 (1994).

Azaryan, A.V. and Vivian Y.H. Hook, "Distinct Properties of Prohormone Thiol Protease (PTP) Compared to Cathepsins B, L, and H: Evidence for PTP as a Novel Cysteine Protease", *Arch. Biochem. Biophys.*, 314: 171–177 (1994).

Schiller, M.R. et al., "'Prohormone Thiol Protease'(PTP) Processing of Recombinant Proenkephalin", *Biochemistry*, 34: 7988–7995 (1995).

*Primary Examiner*—David Guzo
*Assistant Examiner*—Andrew Wang
*Attorney, Agent, or Firm*—Danielle M. Pasqualone, Ph.D.; Incyte Pharmaceuticals, Inc.

[57] ABSTRACT

The present invention provides a polynucleotide (ncp) which identifies and encodes a novel cysteine protease (NCP) expressed in cells of both the adrenal gland and human umbilical vein endothelium. The present invention also provides for antisense molecules and oligomers designed from the nucleotide sequence or its antisense. The invention further provides genetically engineered expression vectors and host cells for the production of purified NCP peptide, antibodies capable of binding to NCP, inhibitors which bind to NCP and pharmaceutical compositions based on NCP specific antibodies or inhibitors. The invention specifically provides for diagnostic assays based on altered ncp expression and which allow identification of such a condition. These assays utilize probes designed from ncp encoding or controlling nucleic acid sequences or antibodies specific for the NCP.

6 Claims, 8 Drawing Sheets

```
                    11              20              29              38              47              56
5' TTC GGC ACG AGG CCT GCC ACA GGT GTC TGC AAT TGA ACT CCA AGG TGC AGA ATG
   F   G   T   R   P   A   T   G   V   C   N   *   T   P   R   C   R   M 65              74              83              92             101             110
   GTT TGG AAA GTA GTT GTA TTC CTC AGT GTG GCC CTG GGA ATT GGT GCC GTT CCT
   V   W   K   V   V   V   F   L   S   V   A   L   G   I   G   A   V   P 119             128             137             146             155             164
   ATA GAT GAT CCT GAA GAT GGA GGC AAG CAC TGG GTG GTG ATC GTG GCA GGT TCA
   I   D   D   P   E   D   G   G   K   H   W   V   V   I   V   A   G   S 173             182             191             200             209             218
   AAT GGC TGG TAT AAT TAT AGG CAC CAG GCA GAC GCG TGC CAT GCC TAC CAG TTC
   N   G   W   Y   N   Y   R   H   Q   A   D   A   C   H   A   Y   Q   F 227             236             245             254             263             272
   ATT CAC CGC AAT GGG ATT CCT GCC GAA CAG ATC GTT GTG ATT ATG TAC GAT GAC
   I   H   R   N   G   I   P   A   E   Q   I   V   V   I   M   Y   D   D 281             290             299             308             317             326
   ATA GCT TAC TCT GAA GAC AAT CCC ACT CCA GGA ATT GTG ATC AAC AGG CCC AAT
   I   A   Y   S   E   D   N   P   T   P   G   I   V   I   N   R   P   N 335             344             353             362             371             380
   GGC ACA GAT GTC TAT CAG GGA GTC CCG AAG GAC TAC ACT GGA GAG GAT GTT ACC
   G   T   D   V   Y   Q   G   V   P   K   D   Y   T   G   E   D   V   T 389             398             407             416             425             434
   CCA CAA AAT TTC CTT GTT GTG TTG AGA GGC GAT GCA GAA GCA GTG AAG GGT ATA
   P   Q   N   F   L   V   V   L   R   G   D   A   E   A   V   K   G   I 443             452             461             470             479             488
   GGA TCC CGC AAA GTC CTG AAG AGT GGT CCC CAG GAT CAC GTG TTC ATT TAT TTC
   G   S   R   K   V   L   K   S   G   P   Q   D   H   V   F   I   Y   F 497             506             515             524             533             542
   ACT GAC CAT GGA TCT TCT GGA ATA CTG GTT TTC CCC AAT GAA GAT CTT CAT GTA
   T   D   H   G   S   S   G   I   L   V   F   P   N   E   D   L   H   V
```

FIG. 2A

```
           551           560           569           578           587           596
AAG GAC CTG ATT AAG ACC ACC CAT TAC ATT TTC AAA AAC AAA ATG TAC CGA AAG
 K   D   L   I   K   T   T   H   Y   I   F   K   N   K   M   Y   R   K 605           614           623           632           641           650
ATG GTG TTC TAC ATT GAG GCC TGT GAG TCT GGG TCC ATG ATG AAC CAC CTG CCG
 M   V   F   Y   I   E   A   C   E   S   G   S   M   M   N   H   L   P 659           668           677           686           695           704
GAT AAC ATC AAT GTT TAT GCA ACT ACT GCT GCC AAC CCC AGA GAG TCG TCC TAC
 D   N   I   N   V   Y   A   T   T   A   A   N   P   R   E   S   S   Y 713           722           731           740           749           758
GCC TGT TAC TAT GAT GAG AAG AGG TCC ACG TAC CTG GGG GAC TGG TAC AGC GTC
 A   C   Y   Y   D   E   K   R   S   T   Y   L   G   D   W   Y   S   V 767           776           785           794           803           812
AAC TGG ATG GAA GAC TCG GAC GTG GAA GAT CTG ACT AAA GAG ACC CTG CAC AAG
 N   W   M   E   D   S   D   V   E   D   L   T   K   E   T   L   H   K 821           830           839           848           857           866
CAG TAC CAC CTG GTA AAA TCG CAC ACC AAC ACC AGC CAC GTC ATG CAG TAT GGA
 Q   Y   H   L   V   K   S   H   T   N   T   S   H   V   M   Q   Y   G 875           884           893           902           911           920
AAC AAA ACA ATC TCC ACC ATG AAA GTG ATG CAG TTT CAG GGT ATG AAA CGC AAA
 N   K   T   I   S   T   M   K   V   M   Q   F   Q   G   M   K   R   K 929           938           947           956           965           974
GCC AGT TCT CCC GTC CCC CTA CCT CCA GTC ACA CAC CTT GAC CTC ACC CCC AGC
 A   S   S   P   V   P   L   P   P   V   T   H   L   D   L   T   P   S 983           992          1001          1010          1019          1028
CCT GAT GTG CCT CTC ACC ATC ATG AAA AGG AAA CTG ATG AAC ACC AAT GAT CTG
 P   D   V   P   L   T   I   M   K   R   K   L   M   N   T   N   D   L 1037          1046          1055          1064          1073          1082
GAG GAG TCC AGG CAG CTC ACG GAG GAG ATC CAG CGG TAT CTG GAT GCC AGG CAC
 E   E   S   R   Q   L   T   E   E   I   Q   R   Y   L   D   A   R   H 1091          1100          1109          1118          1127          1136
CTC ATC CGA GGT GAG GTG GAG CAG CTC CTG TCC GAG AGA GCC CCG CTC ACG GGG
 L   I   R   G   E   V   E   Q   L   L   S   E   R   A   P   L   T   G 1145          1154          1163          1172          1181          1190
CAC AGC TGC TAC CCA GAG GTC CTG TTG TAC TTC CGG ACC CAC TGC TTC AAC TGG
 H   S   C   Y   P   E   V   L   L   Y   F   R   T   H   C   F   N   W
```

FIG. 2B

```
      1199          1208          1217          1226          1235          1244
TAC TCC CCC ACG TAC GAG TTA TGT GTT GAG ACA TTT TGT ACG TGT TGG TCA ACC
 Y   S   P   T   Y   E   L   C   V   E   T   F   C   T   C   W   S   T 1253          1262          1271          1280          1289          1298
TTT GTG AGA AGG CGC TTC CAC TTC ACA GGA TAT AAT TGT CCA TGG CCC ACG TGT
 F   V   R   R   R   F   H   F   T   G   Y   N   C   P   W   P   T   C 1307          1316          1325          1334          1343          1352
GCC TTG GTC ACT ACT GAA GAG CTG CCT CCT GGA AGC TTT TCC CAA GTG TGA GCG
 A   L   V   T   T   E   E   L   P   P   G   S   F   S   Q   V   *   A 1361          1370          1379          1388          1397          1406
CCC CCA CCG GCT GTG TTC TTG ATC AAG AGA CTG GAG AGG TGG AGT GAG AAG TCT
 P   P   P   A   V   F   L   I   K   R   L   E   R   W   S   E   K   S 1415          1424          1433          1442          1451          1460
CCG CTG CTC GGG CCC TCC TGG GGG ACC CCC CGC TCC AGG GCT CGC TCC AGG ACC
 P   L   L   G   P   S   W   G   T   P   R   S   R   A   R   S   R   T 1469          1478          1487          1496          1505          1514
TTC TTC ACA AGA TGA CTT GCT CGC TGT TAC CTG CTT CCC CAG TCT TTT CTG AAA
 F   F   T   R   *   L   A   R   C   Y   L   L   P   Q   S   F   L   K 1523          1532          1541          1550          1559          1568
AAC TAC AAA TTA GGG TGG GAA AAG CTC TGT ATT GAG AAG GGT CAT ATT TGC TTT
 N   Y   K   L   G   W   E   K   L   C   I   E   K   G   H   I   C   F 1577          1586          1595          1604          1613          1622
CTA GGA GGT TTG TTG TTT TGC CTG TTA GTT TTG AGG AGC AGG AAG CTC ATG GGG
 L   G   G   L   L   F   C   L   L   V   L   R   S   R   K   L   M   G 1631          1640          1649          1658          1667          1676
GCT TCT GTA GCC CCT CTC CAA AGG AGT CTT TAT TCT GAG AAT TTG AAG CTG AAA
 A   S   V   A   P   L   Q   R   S   L   Y   S   E   N   L   K   L   K 1685          1694          1703          1712          1721          1730
CCT CTT TAA ATC TTC AGA ATG ATT TTA TTG AAG AGG GCC GCA AGC CCC AAA TGG
 P   L   *   I   F   R   M   I   L   L   K   R   A   A   S   P   K   W
```

FIG. 2C

```
     1739           1748            1757           1766           1775          1784
AAA ACT GTT TTT AGA AAA TAT GAT GAT TTT TGA TTG CTT TTG TAT TTA ATT CTG
 K   T   V   F   R   K   Y   D   D   F   *   L   L   L   Y   L   I   L 1793           1802            1811           1820           1829          1838
CAG GTG TTC AAG TCT TAA AAA ATA AAG ATT TAT AAC AGA ACC CCA AAA AAA AAA
 Q   V   F   K   S   *   K   I   K   I   Y   N   R   T   P   K   K   K

1847
AAA AAA AAA AAA AAA AA 3'
 K   K   K   K   K
```

FIG. 2D

```
            10               20              30
  1  MFYSIFFIHILRIVLVDCNEYSEENVDDRH  SCHISTOMA HEMOGLOBINASE
  1  MVWKV--VVFLSVALGIGAVPIDDPEDGGK  100877

40               50              60
 31  KWAVLVAGSNGFENYRHQADVCHAYHVLLS  SCHISTOMA HEMOGLOBINASE
 29  HWVVIVAGSNGWYNYRHQADACHAYQFIHR  100877

70               80              90
 61  KGVKPEHIITFMYDDIAHNKENPFPGKIFN  SCHISTOMA HEMOGLOBINASE
 59  NGIPAEQIVVIMYDDIAYSEDNPTPGIVIN  100877

100              110             120
 91  DYRHKDYYKGVVIDYKGKKVNPKTFLQVLK  SCHISTOMA HEMOGLOBINASE
 89  RPNGTDVYQGVPKDYTGEDVTPQNFLVVLR  100877

130              140             150
121  GDKRA-----GGKVLKSGKNDDVFIYFTDH  SCHISTOMA HEMOGLOBINASE
119  GDAEAVKGIGSRKVLKSGPQDHVFIYFTDH  100877

160              170             180
146  GAPGILAFPDDDLHAKPFINTLKYLRQHRR  SCHISTOMA HEMOGLOBINASE
149  GSSGILVFPNEDLHVKDLIKTTHYIFKNKM  100877

190              200             210
176  YSKLVIYVEACESGSMFAGLLPTDINIYAT  SCHISTOMA HEMOGLOBINASE
179  YRKMVFYIEACESGSMMNHL-PDNINVYAT  100877

220              230             240
206  TAARPDESSYATFCDDPRISSCLADLYSYD  SCHISTOMA HEMOGLOBINASE
208  TAANPRESSYACYYDEKR-STYLGDWYSVN  100877

250              260             270
236  WIVDSEKHQLTQRTLDQQYKEVKFETNLSH  SCHISTOMA HEMOGLOBINASE
237  WMEDSDVEDLTKETLHKQYHLVKSHTNTSH  100877
```

FIG. 3A

```
266  VQRYGDKKMGKLYLSEFQGSRKKASTEHDE  SCHISTOMA HEMOGLOBINASE
267  VMQYGNKTISTMKVMQFQGMKRKASSPVPL  100877

296  PPMKPKDSIPSRDIPLHTLHRRIMMANNMN  SCHISTOMA HEMOGLOBINASE
297  PPVTHLDLTPSPDMPLTIMKRKLMNTNDLE  100877

326  DKTLLMKILGLKLKRRDLIKDTMEVIDQFM  SCHISTOMA HEMOGLOBINASE
327  ESRQLTEEIQRYLDARHLIRGEVEQ----L  100877

356  FNVKQPNSNATIDETMDCIEVVYKEFQSKC  SCHISTOMA HEMOGLOBINASE
353  LSERAPLTGHS-----CYPEVLLYFRTHC   100877

386  FK-IQQAPEI---------TGYLSTLYNY-  SCHISTOMA HEMOGLOBINASE
377  FNWYSPTYELCVETFCTCWSTFVRRRFHFT  100877

405  --------CQKGYSAENINGVIRKVCG     SCHISTOMA HEMOGLOBINASE
407  GYNCPWPTCALVTTEELPPGSFSQV       100877
```

FIG. 3B

HUMAN CYSTEINE PROTEASE

This application is a divisional application of U.S. application Ser. No. 08/928,613, filed Sep. 12, 1997, now U.S. Pat. No. 5,840,562.

FIELD OF THE INVENTION

The present invention relates to novel, human cysteine protease and the use of its nucleic acid and amino acid sequences in the diagnosis, study, prevention and treatment of autoimmune or degenerative diseases.

BACKGROUND OF THE INVENTION

Cysteine proteases are involved in diverse cellular processes ranging from the processing of precursor proteins to intracellular degradation. They may induce vascular permeability through activation of the kallikrein/kinin pathway, complex with various hemagglutinins, activate complement components and destroy serpins. Their endopeptidase activity and "trypsin-like" specificity leads to the speculation that there are many specialized cysteine protease molecules found in various human cells and tissues.

Cysteine proteases are known to be produced by monocytes, macrophages and other cells of the immune system. These cells migrate to sites of inflammation and in their protective role secrete various molecules which clean up damaged tissue. Under other conditions, these same cells may overproduce the same molecules and cause tissue destruction. This is the case in autoimmune diseases such as rheumatoid arthritis, when the secretion of the cysteine protease, cathepsin C, degrades collagen, laminin, elastin and other structural proteins found in the extracellular matrix of bones. Bone weakened by such degradation is more susceptible to tumor invasion and metastasis.

The novel human cysteine protease of this application was first identified among the sequences of a cDNA library made from human adrenal glands.

Human adrenal glands are cap-like structures located above each kidney. Each gland consists of the adrenal medulla and the adrenal cortex. The adrenal medulla is made up of chromaffin tissue and mainly secretes norepinephrine (NE) and epinephrine (E). Stimulation of the sympathetic nerves to the adrenal medulla releases these two catecholamines into the blood. NE constricts blood vessels, stimulates cardiac activity, inhibits the gastro-intestinal tract, and dilates the pupils of the eyes. Epinephrine triggers almost the same responses, but it has a stronger effect on cardiac activity and a weaker effect on blood vessels. NE and E supplement the effects of the sympathetic nervous system but appear to have little effect on its function.

The adrenal cortex uses cholesterol to produce a large number of corticosteroids which display hormonal activity. The outer layer of the adrenal gland mainly produces the mineralocorticoid, aldosterone. The stimulatory and inhibitory regulation of aldosterone secretion is governed by potassium level, renin-angiotensin interactions, and secretion of adrenocorticotrophic hormone (ACTH), dopamine, serotonin, and β-endorphin. Aldosterone regulates extracellular fluid volume and sodium/potassium balance by interacting with type-I mineralocorticoid receptors in target tissues such as the kidney, salivary gland, and intestinal mucosa.

The inner layers of the adrenal gland are sites of glucocorticoid and androgen, estrogen and progesterone biosynthesis. The principal glucocorticoid is cortisol which functions in the regulation of protein, carbohydrate, lipid, and nucleic acid metabolism, acts as an anti-inflammatory, and plays a biofeedback role in suppressing endocrine functions. Androgen, secreted under the regulation of ACTH, is responsible for initiating the development of secondary sexual characteristics (in both sexes), of sex organs in the male, and for maintaining lifelong spermatogenesis.

Conditions, diseases and disorders of the adrenal gland include chromaffin cell tumors, which are part of the multiple endocrine neoplasia syndromes; Sipple's syndrome, which may be found alone or associated with medullary thyroid carcinoma and parathyroid adenomas; adrenal virilism; Cushing's syndrome; Conn's syndrome; Addison's disease, which is a primary adrenocortical insufficiency; secondary adrenocortical insufficiency, and adrenal adenomas, which include benign adrenal cysts, nonfunctional adrenal carcinoma, and tuberculosis of the adrenal gland.

The adrenal gland and its diseases are reviewed, inter alia, in Guyton AC (1991) *Textbook of Medical Physiology,* W B Saunders Co, Philadelphia Pa.; Isselbacher, K J et al (1994) *Harrison's Principles of Internal Medicine,* McGraw-Hill New York N.Y.; *The Merck Manual of Diagnosis and Therapy* (1992) Merck Research Laboratories, Rahway N.J.; and Goodman A G et al. (1993) *The Pharmacological Basis of Therapeutics,* McGraw-Hill, New York N.Y.

SUMMARY OF THE INVENTION

The present invention relates to a novel cysteine protease (NCP) isolated from human adrenal gland and human umbilical vein endothelial cells (HUVEC) and to the use of this novel protein and its nucleic acid sequences in the diagnosis, study, prevention and treatment of immune diseases, particularly autoimmune and degenerative diseases. The subject invention provides a unique nucleotide sequence (SEQ ID NO 1) which encodes a novel human cysteine protease. This cysteine protease (ncp) was first identified as a partial nucleotide sequence, Incyte Clone 100877, via computer search for local sequence alignments among the cDNAs of an adrenal gland library. The pertinent amino acid residues which allow this molecule to be characterized as a cysteine protease are $Q_{48}$, $C_{52}$ and $H_{150}$. Partial nucleotide sequence was also identified in Incyte Clone 66931 (SEQ ID No 4) from a human umbilical vein endothelial cell cDNA library. A modified XL-PCR procedure, specially designed oligonucleotides and adrenal and Huvec libraries were used to extend Incyte Clones 100877 and 66931 to obtain the full length sequence. Partial nucleotide sequences (SEQ ID Nos 3 and 5–24) disclosed herein, have been identified in several other libraries which appear to share certain features. These features include cell lines or tissues which are immortal (lymphoma and leukemic cell lines), inflamed (adenoid and rheumatoid synovium libraries), or involved in systemic cleanup or defense through either the harboring or production of cells such as monocytes or macrophages (bone marrow, kidney, lung, placenta and small intestine libraries). The assembled nucleotide and amino acid sequences shown in FIG. 1 represent a new human cysteine protease.

An additional computer search for local sequence alignments of the amino acid sequence of the novel cysteine protease described herein showed that the most closely related molecule, approximately 50% amino acid similarity, is the hemoglobinase from *Schistosoma japonicum* (GenBank Accession X70967; Merckelbach A et al (1994) Trop Med Parasitol 45:193 198). The cysteine protease of this application shows 50% amino acid sequence similarity with hemoglobinase from *S. japonicum*. Based on the conserved cysteine protease residues, $Q_{48}$, $C_{52}$ and $H_{150}$, of the catalytic region; the similarity to the closely related molecule, hemoglobinase; and the presence of the novel cysteine protease in cells and defense; which are immortal, inflamed or involved in systemic cleanup or defense; the novel cysteine protease is involved in proteolysis, in systemic cleanup and defense, and is therefore useful in the diagnosis, study, prevention and treatment of autoimmune or degenerative diseases.

Further aspects of the present invention include antisense molecules of ncp which are useful in diminishing or eliminating expression of the genomic nucleotide sequence.

The present invention also relates, in part, to polynucleotide sequences and expression vectors encoding NCP and methods for the production and recovery of NCP from host cells.

The ncp nucleic acid sequences disclosed herein may be used in diagnostic assays to detect and quantify levels of ncp mRNA in cells and tissues. For example, a ncp nucleic acid sequence may be used in PCR or hybridization assays of biopsied fluids or tissues to diagnose abnormalities in gene expression associated with an immune disorder. The invention further relates to diagnostic kits for the detection of NCP or nucleic acid sequences encoding NCP comprising NCP, antibodies specific to NCP or nucleic acid sequences encoding NCP. Such diagnostic kits may be used for the detection of any condition, disorder, or disease state related to aberrant expression of NCP, including but not limited to: anemia, arteriosclerosis, asthma, bronchitis, cancers, emphysema, gingivitis, inflammatory bowel disease, insulin-dependent diabetes mellitus, leukemia, osteoarthritis, osteoporosis, pulmonary fibrosis, rheumatoid arthritis, septic shock syndromes, and systemic lupus erythematosus. Steps for testing a biological sample with nucleotide probes based on the ncp nucleotide sequence or antibodies produced against the purified NCP protein are provided. Antibodies may be used for therapeutic as well as diagnostic purposes, eg, in neutralizing the activity of an NCP associated with an immune disorder such as rheumatoid arthritis. The present invention also relates in part to proteins, peptides, and organic molecules capable of modulating activity of NCP which may be used therapeutically in the treatment of disease states associated with aberrant expression of an NCP. The present invention also relates to pharmaceutical compositions for the treatment of disease states associated with aberrant expression of ncp comprising NCP, nucleic acid sequences encoding NCP, anti NCP or other proteins, peptides or organic molecules capable of modulating NCP expression.

DESCRIPTION OF THE FIGURES

FIGS. 2A, 2B, 2C and 2D show the nucleic acid and amino acid alignments of NCP.

FIGS. 3A and 3B show the amino acid alignments between NCP and hemoglobinase from *Schistosoma japonicum* (GenBank Accession X70967).

DETAILED DESCRIPTION OF THE INVENTION

Definitions

The present invention relates to a novel cysteine protease which is expressed in the adrenal gland, human umbilical vein endothelial cells, lymphoma and leukemic cell lines, adenoid, rheumatoid synovium, bone marrow, kidney, lung, placenta and small intestine. As used herein, the abbreviation for the novel cysteine protease in lower case (ncp) refers to a gene, cDNA, RNA or nucleic acid sequence while the upper case version (NCP) refers to a protein, polypeptide, peptide, oligopeptide, or amino acid sequence.

Figure 1:
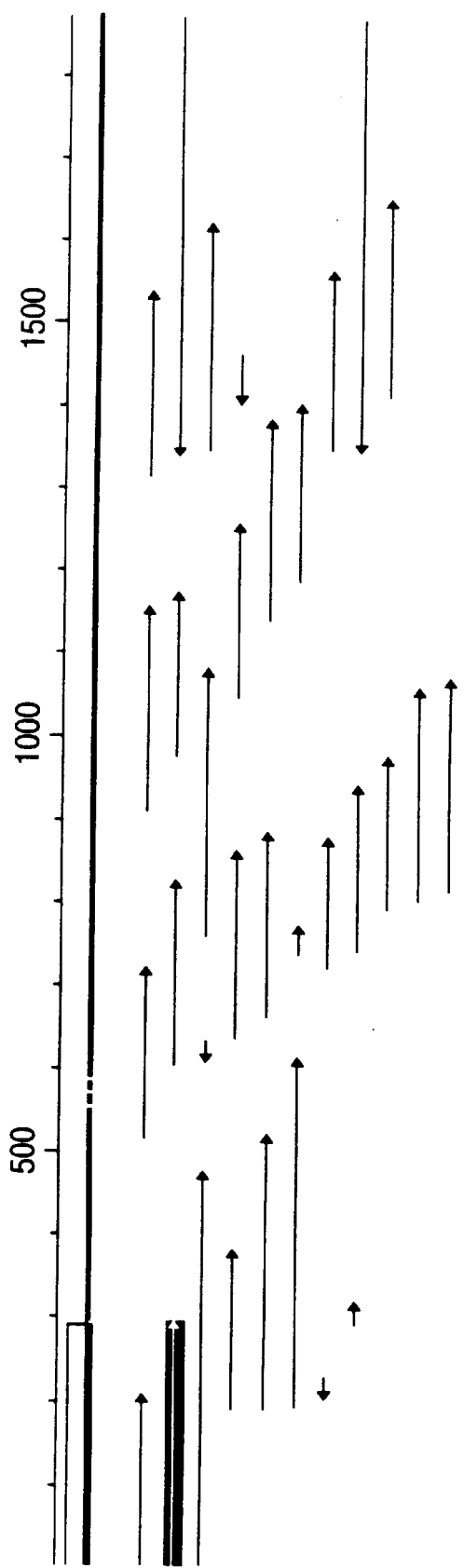
FIG. 1 displays an alignment of cDNA sequences which encompass the coding region of ncp. Alignments shown in this and the following figures were produced using the multisequence alignment program of DNASTAR software (DNASTAR Inc, Madison Wis.).

As used herein, NCP is a term which refers to NCP from any species, including, bovine, ovine, porcine, equine, murine and preferably human. It refers to naturally occurring or variant form and NCP from any source whether natural, semi-synthetic, synthetic or recombinant. A preferred NCP is one having at least 80% amino acid sequence similarity, another preferred variant is one having 90% amino acid sequence similarity, and another preferred variant is one having 95% amino acid sequence similarity to the NCP amino acid sequence illustrated in FIG. 1.

An "oligonucleotide" or "oligomer" is a stretch of nucleotide residues which has a sufficient number of bases to be used in a polymerase chain reaction (PCR). These short sequences are based on (or designed from) genomic or cDNA sequences and are used to amplify, confirm, or reveal the presence of an identical, similar or complementary DNA or RNA in a particular cell or tissue. Oligonucleotides or oligomers comprise portions of a DNA sequence having at least about 10 nucleotides and as many as about 50 nucleotides, preferably about 15 to 30 nucleotides. They are chemically synthesized and may be used as probes.

"Probes" are nucleic acid sequences of variable length, preferably between at least about 10 and as many as about 6,000 nucleotides. They are used in the detection of identical, similar, or complementary nucleic acid sequences. Longer length probes are usually obtained from a natural or recombinant source, are highly specific and much slower to hybridize than oligonucleotides. They may be single- or double-stranded and are carefully designed to have specificity in PCR, hybridization membrane-based, or ELISA-like technologies.

"Reporter" molecules are chemical moieties used for labelling a nucleic or amino acid sequence. They include, but are not limited to, radionuclides, enzymes, fluorescent, chemiluminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI and Hind III or which provide a blunt end such as EcoRV, SnaBI and StuI.

"Control elements" or "regulatory sequences" are those nontranslated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signalling, etc.

"Active" refers to those forms, fragments, or domains of an amino acid sequence which display the biologic and/or immunogenic activity characteristic of the naturally occurring peptide.

"Naturally occurring NCP" refers to a polypeptide produced by cells which have not been genetically engineered or which have been genetically engineered to produce the same sequence as that naturally produced. Specifically contemplated are various polypeptides which arise from post-transnational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring NCP by amino acid insertions, deletions and/or substitutions, created using recombinant DNA techniques. Guidance in determining which amino acid residues may be replaced, added or deleted without abolishing characteristics of interest may be found by comparing the sequence of NCP with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the ncp sequence using recombinant DNA techniques.

A "signal or leader sequence" is a short amino acid sequence which can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and either the same length as or considerably shorter than a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and their derivatives.

A "standard" is a quantitative or qualitative measurement used for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

"Animal" as used herein may be defined to include human, domestic (cats, dogs, etc), agricultural (cows, horses, sheep, goats, chicken, fish, etc) or test species (frogs, mice, rats, rabbits, simians, etc).

"Conditions" includes cancers, disorders or diseases in which ncp activity may be implicated. These specifically include, but are not limited to, anemia, arteriosclerosis, asthma, bronchitis, emphysema, gingivitis, inflammatory bowel disease, insulin-dependent diabetes mellitus leukemia, multiple endocrine neoplasias, osteoarthritis, osteoporosis, pulmonary fibrosis, rheumatoid arthritis, septic shock syndromes, and systemic lupus erythematosus.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

Description of the Invention

The present invention provides for a purified polynucleotide which encodes a novel cysteine protease homolog which is expressed in human cells or tissue. The novel cysteine protease (ncp; Incyte Clone 100877) was first identified among the cDNAs from an adrenal gland cDNA library. The amino acid residues which allow this molecule to be characterized as a cysteine protease are $Q_{48}$, $C_{52}$ and $H_{150}$. The number of nucleotides separating the Q and C residues in this novel cysteine protease is fewer than found in other cysteine proteases, such as papain.

In addition, the novel cysteine protease is expressed in human umbilical vein endothelial cells (HUVEC). The full length ncp sequence was obtained by sequencing clones from both the adrenal and the HUVEC cDNA libraries. The molecule most closely related to this cysteine protease is hemoglobinase cloned from the blood fluke, *Schistosoma japonicum*, GenBank Accession X70967 (Merckelbach A et al (1994) Trop Med Parasitol 45:193 198). The ncp of the present application may well be human hemoglobinase even though it has not been found in either spleen or liver libraries where a hemoglobinase would likely be active. It was, however, found in numerous tissues in which systemic cleanup or defense had been activated and where hemoglobinase or an NCP might be expected to act proteolytically to clean up the contents of injured or dying red blood cells.

Transcripts which did align with some portion of the ncp molecule were found in other Incyte cDNA libraries. Thirty-two segments of cDNAs from different Incyte Clones are shown as an overlapping assemblage in FIG. 1. Twenty three of these Incyte Clones including cDNAs from U937 cell, THP-1 cell, rheumatoid synovium, bone marrow, kidney, lung, inflamed adenoid, placenta, and small intestine libraries are presented in the Sequence Listing. In fact, ncp is fairly common in libraries where the normal tissue functions in, and the role of the molecule, proteolytic activity, would appear to be associated with, for the purpose of systemic cleanup and defense.

Purified nucleotide sequences, such as ncp, have numerous applications in techniques known to those skilled in the art of molecular biology. These techniques include their use as PCR or hybridization probes, for chromosome and gene mapping, in the production of sense or antisense nucleic acids, in screening for new therapeutic molecules, etc. These examples are well known and are not intended to be limiting. Furthermore, the nucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

As a result of the degeneracy of the genetic code, a multitude of NCP-encoding nucleotide sequences may be produced and some of these will bear only minimal homology to the endogenous sequence of any known and naturally occurring cysteine protease sequence. This invention has specifically contemplated each and every possible variation of nucleotide sequence that could be made by selecting combinations based on possible codon choices. These combinations are made in accordance with the standard triplet genetic code as applied to the nucleotide sequence of naturally occurring NCP and all such variations are to be considered as being specifically disclosed.

Although the ncp nucleotide sequence and its derivatives or variants are preferably capable of identifying the nucleotide sequence of the naturally occurring NCP under optimized conditions, it may be advantageous to produce NCP-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding the NCP without altering the encoded amino acid sequence include the production of RNA transcripts having more desirable properties, such as a longer half-life, than transcripts produced from the naturally occurring sequence.

Nucleotide sequences encoding NCP may be joined to a variety of other nucleotide sequences by means of well established recombinant DNA techniques (Sambrook J et al (1989) *Molecular Cloning: A Laboratory Manual*, Cold Spring Harbor Laboratory, Cold Spring Harbor N.Y.; or Ausubel F M et al (1989) *Current Protocols in Molecular Biology*, John Wiley & Sons, New York City). Useful sequences for joining to ncp include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 provides additional uses for oligonucleotides based upon the ncp nucleotide sequence. Such oligomers are generally chemically synthesized, but they may be of recombinant origin or a mixture of both. Oligomers generally comprise two nucleotide sequences, one with sense orientation (5'→3') and one with antisense (3' to 5') employed under optimized conditions for identification of a specific gene or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. Gobinda et al (1993; PCR Methods Applic 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase. Gobinda et al present data concerning Factor IX for which they identified a conserved stretch of 20 nucleotides in the 3' noncoding region of the gene.

Inverse PCR is the first method to report successful acquisition of unknown sequences starting with primers based on a known region (Triglia T et al (1988) Nucleic Acids Res 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al, supra).

Capture PCR (Lagerstrom M et al (1991) PCR Methods Applic 1:111–19) is a method for PCR amplification of DNA fragments adjacent to a known sequence in human and YAC DNA. As noted by Gobinda et al (supra), capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker J D et al (1991; Nucleic Acids Res 19:3055–60), teach walking PCR, a method for targeted gene walking which permits retrieval of unknown sequence. In this same vein, PromoterFinder™ a new kit available from Clontech (Palo Alto Calif.) uses PCR and primers derived from p53 to walk in genomic DNA. Nested primers and special PromoterFinder libraries are used to detect upstream sequences such as promoters and regulatory elements. This process avoids the need to screen libraries and is useful in finding intron/exon junctions.

Another new PCR method, "*Improved Method for Obtaining Full Length cDNA Sequences*" by Guegler et al, patent application Ser. No 08/487,112, filed Jun. 7, 1995 and hereby incorporated by reference, employs XL-PCR™ (Perkin-Elmer, Foster City Calif.) to amplify and extend partial nucleotide sequence into longer pieces of DNA. This method was developed to allow a single researcher to process multiple genes (up to 20 or more) at one time and to obtain an extended (possibly full-length) sequence within 6–10 days. This new method replaces methods which use labelled probes to screen plasmid libraries and allow one researcher to process only about 3–5 genes in 14–40 days.

In the first step, which can be performed in about two days, any two of a plurality of primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg Md.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

A new method for analyzing either the size or the nucleotide sequence of PCR products is capillary electrophoresis. Systems for rapid sequencing are available from Perkin Elmer (Foster City Calif.), Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Another aspect of the subject invention is to provide for ncp hybridization probes which are capable of hybridizing with naturally occurring nucleotide sequences encoding NCP. The stringency of the hybridization conditions will determine whether the probe identifies only the native nucleotide sequence of ncp or sequences of other closely related cysteine protease molecules. If degenerate ncp nucleotide sequences of the subject invention are used for the detection of related cysteine protease encoding sequences, they should preferably contain at least 50% of the nucleotides of the sequences presented herein. Hybridization probes of the subject invention may be derived from the nucleotide sequences of the SEQ ID NOs 1–24 or from surrounding genomic sequences comprising untranslated regions such as promoters, enhancers and introns. Such hybridization probes may be labelled with appropriate reporter molecules.

Means for producing specific hybridization probes for cysteine proteases include oligolabelling, nick translation, end-labelling or PCR amplification using a labelled nucleotide. Alternatively, the cDNA sequence may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides. A number of companies (such as Pharmacia Biotech, Piscataway N.J.; Promega, Madison Wis.; US Biochemical Corp, Cleveland, Ohio; etc.) supply commercial kits and protocols for these procedures.

It is also possible to produce a DNA sequence, or portions thereof, entirely by synthetic chemistry. Sometimes the source of information for producing this sequence comes from the known homologous sequence from closely related organisms. After synthesis, the nucleic acid sequence can be used alone or joined with a pre-existing sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

The ncp nucleotide sequences can be used individually in a diagnostic test or assay to detect disorder or disease processes associated with abnormal levels of IL expression. The nucleotide sequence is added to a sample (fluid, cell or tissue) from a patient under hybridizing conditions. After an incubation period, the sample is washed with a compatible fluid which optionally contains a reporter molecule which will bind the specific nucleotide. After the compatible fluid is rinsed off, the reporter molecule is quantitated and compared with a standard for that fluid, cell or tissue. If ncp expression is significantly different from the standard, the assay indicates the presence of disorder or disease. The form of such qualitative or quantitative methods may include northern analysis, dot blot or other membrane-based technologies, dip stick, pin or chip technologies, PCR, ELISAs or other multiple sample format technologies.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by a disorder or disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the efficacy of treatment over a period of several days or several months.

The nucleotide sequence for ncp can also be used to generate probes for mapping the native genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques,* Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal and carrier or affected individuals.

The nucleotide sequence encoding NCP may be used to produce an amino acid sequence using well known methods of recombinant DNA technology. Goeddel (1990, *Gene Expression Technology, Manual and Enzymology,* Vol 185, Academic Press, San Diego Calif.) is one among many publications which teach expression of an isolated, purified nucleotide sequence. The amino acid or peptide may be expressed in a variety of host cells, either prokaryotic or eukaryotic. Host cells may be from the same species from which the nucleotide sequence was derived or from a different species. Advantages of producing an amino acid sequence or peptide by recombinant DNA technology include obtaining adequate amounts for purification and the availability of simplified purification procedures.

Cells transformed with ncp nucleotide sequence may be cultured under conditions suitable for the expression and recovery of peptide from cell culture. The peptide produced by a recombinant cell may be secreted or may be contained intracellularly depending on the sequence and/or the vector used. In general, it is more convenient to prepare recombinant proteins in secreted form, and this is accomplished by ligating ncp to a recombinant nucleotide sequence which directs its movement through a particular prokaryotic or eukaryotic cell membrane. Other recombinant constructions may join ncp to nucleotide sequence encoding a polypeptide domain which will facilitate protein purification (Kroll D J et al (1993) DNA Cell Biol 12:441–53).

Direct peptide synthesis using solid-phase techniques (Stewart et al (1969) *Solid-Phase Peptide Synthesis,* W H Freeman Co, San Francisco Calif.; Merrifield J (1963) J Am Chem Soc 85:2149–2154) is an alternative to recombinant or chimeric peptide production. Automated synthesis may be achieved, for example, using Applied Biosystems 431A Peptide Synthesizer in accordance with the instructions provided by the manufacturer. Additionally NCP or any part thereof may be mutated during direct synthesis and combined using chemical methods with other cysteine protease sequences or any part thereof.

Although an amino acid sequence or oligopeptide used for antibody induction does not require biological activity, it must be immunogenic. NCP used to induce specific antibodies may have an amino acid sequence consisting of at least five amino acids and preferably at least 10 amino acids. Short stretches of amino acid sequence may be fused with those of another protein such as keyhole limpet hemocyanin, and the chimeric peptide used for antibody production. Alternatively, the peptide may be of sufficient length to contain an entire domain.

Antibodies specific for NCP may be produced by inoculation of an appropriate animal with an antigenic fragment of the peptide. An antibody is specific for NCP if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R et al (1989) PNAS 86:3833–3837, or Huse W D et al (1989) Science 256:1275–1281), or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules which specifically bind NCP. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of NCP active in normal, diseased, or therapeutically treated cells or tissues.

The examples below are provided to illustrate the subject invention. These examples are provided by way of illustration and are not included for the purpose of limiting the invention.

EXAMPLES

I Adrenal Gland cDNA Library Construction

Although both the adrenal gland and human umbilical vein endothelial cell cDNA libraries were employed to clone the full length gene; for purposes of example, the adrenal gland cDNA library construction will be described.

The adrenal gland cDNA library was constructed from a pooled sample of five, whole, normal adrenal glands from Caucasian males and females who ranged in age from 10 to 46 years. The poly A+ RNA was obtained from Clontech Laboratories Inc (Catalogue #6571-2; Palo Alto Calif.)

Stratagene (La Jolla Calif.) made the cDNA library using this poly A+ RNA. The cDNA synthesis was primed using both oligo dT and random hexamers, and the two cDNA libraries were treated separately. Synthetic adapter oligonucleotides were ligated onto the ends of the cDNAs enabling their insertion into the Uni-ZAP™ vector system (Stratagene).

The pBluescript™ phagemid (Stratagene) cDNA clones were obtained by the in vivo excision process, and phagemids from the two cDNA libraries were combined into a single library by mixing equal numbers of bacteriophage. The latter were used to transform *E. coli* host strain XL1-Blue™ (Stratagene). Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the β-lactamase gene on the phagemid allowed transformed bacteria to grow on medium containing ampicillin.

II Isolation of cDNA Clones

Phagemid DNAs containing the cDNA insert may be purified using the QIAWELL-8 Plasmid Purification System from QIAGEN Inc (Chatsworth Calif.). This high-throughput method isolates highly purified phagemid DNA from lysed bacterial cells using QIAGEN anion-exchange resin particles and EMPORE™ membrane technology from 3M (Minneapolis Minn.) in a multiwell format. The DNA was eluted and prepared for DNA sequencing and other analytical manipulations.

III Sequencing of cDNA Clones

The cDNA inserts from random isolates of the adrenal gland library were sequenced in part. Methods for DNA sequencing are well known in the art and employ such enzymes as the Klenow fragment of DNA polymerase I, SEQUENASE™ (US Biochemical Corp) or Taq polymerase. Methods to extend the DNA from an oligonucleotide primer annealed to the DNA template of interest have been developed for both single- and double-stranded templates. Chain termination reaction products were separated using electrophoresis and detected via their incorporated, labelled precursors. Recent improvements in mechanized reaction preparation, sequencing and analysis have permitted expansion in the number of sequences that can be determined per day. Preferably, the process is automated with machines such as the Applied Biosystems Catalyst 800 and 373 DNA sequencers.

The quality of any particular cDNA library may be determined by performing a pilot scale analysis of the cDNAs and checking for percentages of clones containing vector, lambda or *E. coli* DNA, mitochondrial or repetitive DNA, and clones with exact or homologous matches to public databases. The number of unique sequences, those having no known match in any available database, are then recorded.

IV Homology Searching of cDNA Clones and Their Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. While it is useful for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Figure 4:
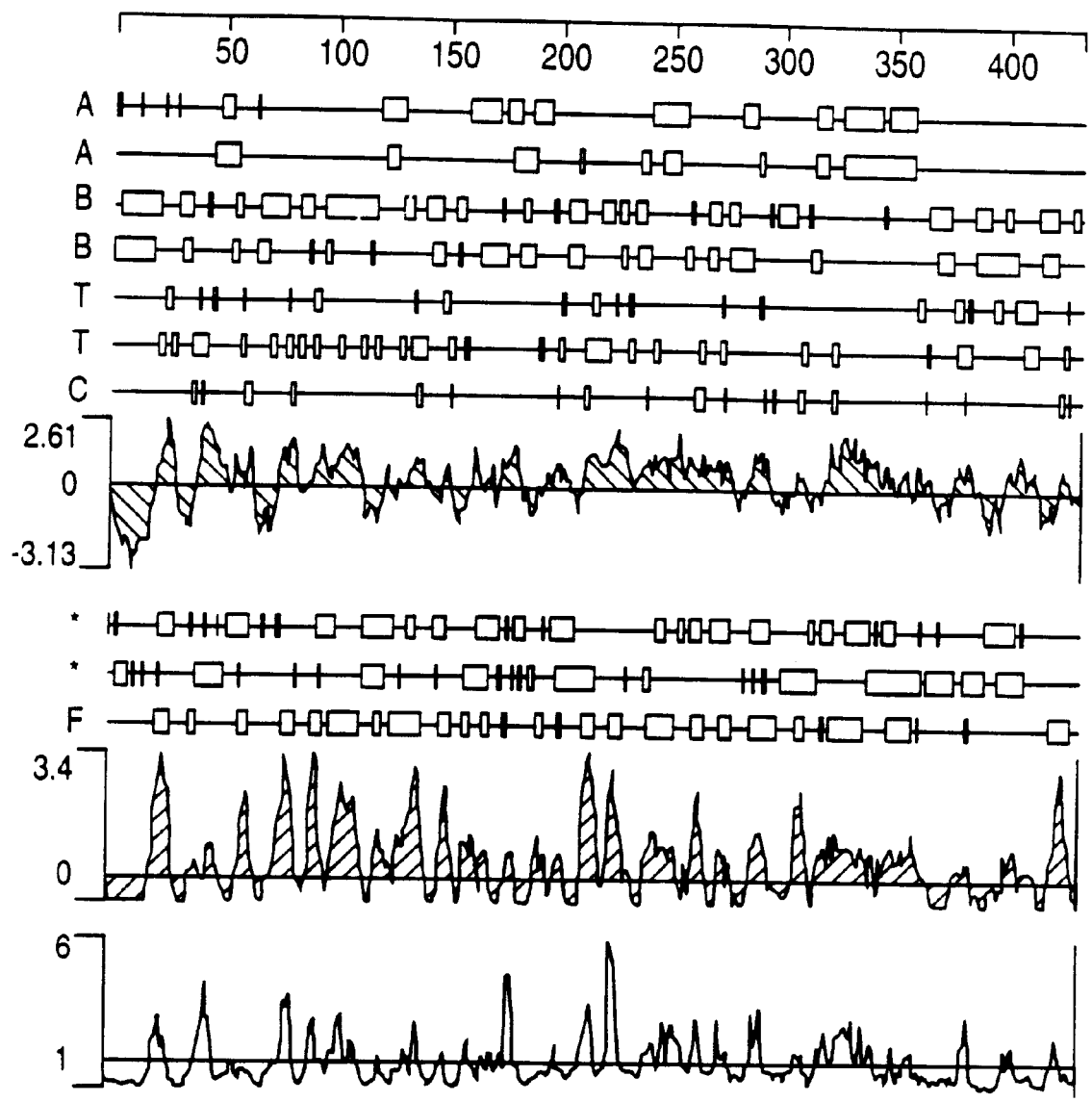
FIG. 4 displays the DNASTAR analysis of NCP α regions (A), β regions (B), turn regions (T), coil regions (C), hydrophilicity plot (H), α amphipathic regions (AA), β amphipathic regions (BA), antigenic index (AI) and surface probability plot (S) based on the predicted acid amino sequence and composition.

Using the criteria described above, the following partial novel cysteine protease molecules were identified and are disclosed herein: Incyte Clone 1098 (SEQ ID NO 3) from the U937 (a histiocytic lymphoma cell line) library, Incyte Clone 75848 (SEQ ID NO 5) from the THP-1 (a leukemic monocyte cell line) library, Incyte Clones 77015 (SEQ ID NO 6), 77424 (SEQ ID NO 7), 77645 (SEQ ID NO 8), 77651 (SEQ ID NO 9), and 78547 (SEQ ID NO 10) from the rheumatoid synovium library, Incyte Clone 104286 (SEQ ID NO 11) from the bone marrow library, Incyte Clone 115565 (SEQ ID NO 12) from the kidney library, Incyte Clones 125569 (SEQ ID NO 13) and 125830 (SEQ ID NO 14) from the lung library, Incyte Clones 158868 (SEQ ID NO 15) and 162199 (SEQ ID NO 16) from the inflamed adenoid library, Incyte Clones 172449 (SEQ ID NO 17) and 174690 (SEQ ID NO 18) from the bone marrow library, Incyte Clones 180594 (SEQ ID NO 19) and 180935 (SEQ ID NO 20) from the placenta library, Incyte Clone 190299 (SEQ ID NO 21) from the rheumatoid synovium library, Incyte Clones 195541 (SEQ ID NO 22) and 197617 (SEQ ID NO 23) from the kidney library, and Incyte Clone 238970 (SEQ ID NO 24) from the small intestine library. The full length nucleic and amino acid sequences for this novel human cysteine protease are shown in FIGS. 2A, 2B, 2C and FIG. 2D. FIGS. 3A and 3B show the alignment between the translated amino acid sequence for ncp and the closest related cysteine protease, hemoglobinase from Schistosoma japonicum (GenBank Accession X70967; Merckelbach A et al (1994) Trop Med Parasitol 45:193 198) . As previously described, FIG. 4 shows various parameters (hydrophilicity, etc) of the enzyme.

Extension of cDNAs to Full Length

The Incyte clones presented here can be and were used to design oligonucleotide primers for extension of the cDNAs to full length. Primers are designed based on known sequence; one primer is synthesized to initiate extension in the antisense direction (XLR) and the other to extend sequence in the sense direction (XLF). The primers allow the sequence to be extended "outward" generating amplicons containing new, unknown nucleotide sequence for the gene of interest. The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations was avoided.

The adrenal cDNA library was used with XLR=GGT GAA TGA ACT GGT AGG CAT GG and XLF=AAT CCC ACT CCA GGA ATT GTG ATC primers to extend and amplify Incyte Clone 100877. Using a second set of primers, XLR=ACC CAG ACT CAC AGG CTT CAA TG and XLF=GGG GAC TGG TAC AGC GTC AAC TG and the HUVEC cDNA library, Incyte Clone 66931 was extended to obtain the remaining portion of the cysteine protease sequence.

By following the instructions for the XL-PCR kit and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Although all extensions potentially contain a full length gene, some of the largest products or bands are selected and cut out of the gel. Further purification involves using a commercial gel extraction method such as QIAQuick™ (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer. Then, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, 12 colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Diagnostic Assay Using NCP Specific Oligomers

In those cases where a specific condition (see definitions supra) is suspected to involve altered quantities of ncp, oligomers may be designed to establish the presence and/or quantity of mRNA expressed in a biological sample. There are several methods currently being used to quantitate the expression of a particular molecule. Most of these methods use radiolabelled (Melby P C et al 1993 J Immunol Methods 159:235–44) or biotinylated (Duplaa C et al 1993 Anal Biochem 229–36) nucleotides, coamplification of a control nucleic acid, and standard curves onto which the experimental results are interpolated. Quantitation may be speeded up by running the assay in an ELISA format where the oligomer-of-interest is presented in various dilutions and a colorimetric response gives rapid quantitation. For example, NCP deficiency may result in an abundance of the proinflammatory interleukin molecules, much swelling and discomfort. In like manner, overexpression may cause apoptosis and major tissue damage. In either case, a quick diagnosis may allow health professionals to treat the condition and prevent worsening of the condition. This same assay can be used to monitor progress of the patient as his/her physiological situation moves toward the normal range during therapy.

VII Sense or Antisense Molecules

Knowledge of the correct cDNA sequence of this novel cysteine protease or its regulatory elements enable its use as a tool in sense (Youssoufian H and H F Lodish 1993) Mol Cell Biol 13:98–104) or antisense (Eguchi et al (1991) Annu Rev Biochem 60:631–652) technologies for the investigation or alteration of gene expression. To inhibit in vivo or in vitro ncp expression, an oligonucleotide based on the coding sequence of a fragment of an ncp designed using Oligo 4.0 (National Biosciences Inc) may be used. Alternatively, a fragment of an ncp produced by digesting ncp coding sequence with restriction enzymes selected to digest the ncp at specific restriction sites using Inherit Analysis software (Applied Biosystems) may be used to inhibit ncp expression. Furthermore, antisense molecules can be designed to inhibit promoter binding in the upstream nontranslated leader or at various sites along the ncp coding region. Alternatively, antisense molecules may be designed to inhibit translation of an mRNA into polypeptide by preparing an oligomer or fragment which will bind in the region spanning approximately −10 to +10 nucleotides at the 5' end of the coding sequence. These technologies are now well known in the art.

In addition to using fragments constructed to interrupt transcription of the open reading frame, modifications of gene expression can be obtained by designing antisense sequences to enhancers, introns, or even to transacting regulatory genes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Any of these types of antisense molecules may be placed in expression vectors and used to transform preferred cells or tissues. This may include introduction of the expression vector into a synovial cavity for transient or short term therapy. Expression of the antisense sequence would continue to flood the cell with inhibitory molecules until all copies of the vector were disabled by endogenous nucleases. Such transient expression may last for a month or more with a non replicating vector and three months or more if appropriate replication elements are used in the transformation or expression system.

Stable transformation of appropriate dividing cells with a vector containing the antisense molecule can produce a transgenic cell line, tissue or organism (see, for example, Trends in Biotechnol 11:155–215 (1993) and U.S. Pat. No. 4,736,866, Apr. 12, 1988). Those cells which assimilate or replicate enough copies of the vector to allow stable integration will also produce enough antisense molecules to compromise or entirely eliminate normal activity of the ncp. Frequently, the function of an ncp can be ascertained by observing behaviors such as lethality, loss of a physiological pathway, changes in morphology, etc. at the cellular, tissue or organismal level.

VIII Expression of NCP

Expression of the NCP may be accomplished by subcloning the cDNAs into appropriate vectors and transfecting the vectors into host cells. In this case, the cloning vector previously used for the generation of the tissue library also provides for direct expression of the ncp sequence in *E. coli.* Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods will produce a fusion protein corresponding to the first seven residues of β-galactosidase, about 5 to 15 residues which correspond to linker, and the peptide encoded within the ncp cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide linkers containing cloning sites as well as a stretch of DNA sufficient to hybridize to the end of the target cDNA (25 bases) can be synthesized chemically by standard methods. These primers can then used to amplify the desired gene fragments by PCR. The resulting fragments can be digested with appropriate restriction enzymes under standard conditions and isolated by gel electrophoresis. Alternatively, similar gene fragments can be produced by digestion of the cDNA with appropriate restriction enzymes and filling in the missing gene sequence with chemically synthesized oligonucleotides. Partial nucleotide sequence from more than one cysteine protease homolog can be ligated together and cloned into appropriate vectors to optimize expression.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

If native promoters are not part of the cDNA, other host specific promoters may be specifically combined with the coding region of ncp. They include MMTV, SV40, and metallothionine promoters for CHO cells; trp, lac, tac and T7 promoters for bacterial hosts; and alpha factor, alcohol oxidase and PGH promoters for yeast. In addition, transcription enhancers, such as the rous sarcoma virus (RSV) enhancer, may be used in mammalian host cells. Once homogeneous cultures of recombinant cells are obtained through standard culture methods, large quantities of recombinantly produced peptide can be recovered from the conditioned medium and analyzed using methods known in the art.

IX Isolation of Recombinant NCP

NCP may be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen) between the purification domain and the ncp sequence may be useful to facilitate expression of NCP.

X Cysteine Protease Activity

The activity of purified or expressed NCP may be tested by mixing a known quantity of the enzyme with a proteinaceous matrix material (such as collagen) in a biologically acceptable medium and allowing NCP to carry out digestion for an appropriate period of time. A zymogram, which consists of a nondenaturing polyacrylamide gel soaked in the proteinaceous material onto which various concentrations, preferably between 10 and 100 ng/μl, of NCP are spotted, may be used to demonstrate NCP activity. After 30–60 min, the gel is stained with Coomassie blue. An active enzyme will create spots in which the concentration of protein has been reduced (lighter stain) or completely cleared (Paech et al (1993) Anal Biochem 208:249–54).

XI Identification of or Production of NCP Specific Antibodies

Purified NCP is used to screen a pre-existing antibody library or to raise antibodies using either polyclonal or monoclonal methodology. In a polyclonal approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In a monoclonal approach, the amino acid sequence of NCP, as deduced from translation of the cDNA, is analyzed to determine regions of high immunogenicity. Oligopeptides comprising appropriate hydrophilic regions, as shown in FIGS. 3A and 3B, are synthesized and used in suitable immunization protocols to raise antibodies. Analysis to select appropriate epitopes is described by Ausubel F M et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel F M et al, supra). If necessary, a cysteine may be introduced at the N-terminus of the peptide to permit coupling to KLH. Rabbits are immunized with the peptide-KLH complex in complete Freund's adjuvant The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled NCP to identify those fusions producing the monoclonal antibody with the desired specificity. In a typical protocol, wells of plates (FAST; Becton-Dickinson, Palo Alto, Calif.) are coated with affinity purified, specific rabbit-anti-mouse antibodies (or suitable anti-species Ig) at 10 mg/ml. The coated wells are blocked with 1% BSA, washed and exposed to supernatants from hybridomas. After incubation the wells are exposed to labeled NCP, 1 mg/ml. Clones producing antibodies will bind a quantity of labeled NCP which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, will typically be made by standard procedures as described in Harlow and Lane (1988) *Antibodies: A Laboratory Manual,* Cold Spring Harbor Laboratory, Cold Spring Harbor N.Y.; and in Goding (1986) *Monoclonal Antibodies: Principles and Practice,* Academic Press, New York City, both incorporated herein by reference.

XII Diagnostic Test Using NCP Specific Antibodies

Particular NCP antibodies are useful for the diagnosis of prepathologic conditions, and chronic or acute diseases which are characterized by differences in the amount or distribution of NCP. To date, NCP has been found in many libraries where it is predominantly associated with organ function, inflammation or defense.

Diagnostic tests for NCP include methods utilizing the antibody and a label to detect NCP in human body fluids, tissues or extracts of such tissues. The polypeptides and antibodies of the present invention may be used with or without modification. Frequently, the polypeptides and antibodies will be labeled by joining them, either covalently or noncovalently, with a reporter molecule. A wide variety of labels and conjugation techniques are known and have been reported extensively in both the scientific and patent literature. Suitable reporter molecules or labels include those radionuclides, enzymes, fluorescent, chemiluminescent, or chromogenic agents previously mentioned as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced as shown in U.S. Pat. No. 4,816,567, incorporated herein by reference.

A variety of protocols for measuring soluble or membrane-bound NCP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NCP is preferred, but a competitive binding assay may be employed. These assays are described, among other places, in Maddox, Del. et al (1983, J Exp Med 158:1211).

XII Purification of Native NCP Using Specific Antibodies

Native or recombinant NCP can be purified by immunoaffinity chromatography using antibodies specific for that particular NCP. In general, an immunoaffinity column is constructed by covalently coupling the anti-NCP antibody to an activated chromatographic resin.

Polyclonal immunoglobulins are prepared from immune sera either by precipitation with ammonium sulfate or by purification on immobilized Protein A (Pharmacia Biotech). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia Biotech). The antibody is coupled to the resin, the resin is blocked, and the derivative resin is washed according to the manufacturer's instructions.

Such immunoaffinity columns may be utilized in the purification of NCP by preparing a fraction from cells containing NCP in a soluble form. This preparation may be derived by solubilization of whole cells or of a subcellular fraction obtained via differential centrifugation (with or without addition of detergent) or by other methods well known in the art. Alternatively, soluble NCP containing a signal sequence may be secreted in useful quantity into the medium in which the cells are grown.

A soluble NCP-containing preparation is passed over the immunoaffinity column, and the column is washed under conditions that allow the preferential absorbance of NCP (eg, high ionic strength buffers in the presence of detergent). Then, the column is eluted under conditions that disrupt antibody/NCP binding (eg, a buffer of pH 2–3 or a high concentration of a chaotrope such as urea or thiocyanate ion), and NCP is collected.

XIV Drug Screening

This invention is particularly useful for screening therapeutic compounds by using binding fragments of NCP in any of a variety of drug screening techniques. The peptide fragment employed in such a test may either be free in solution, affixed to a solid support, borne on a cell surface or located intracellularly. One may measure, for example, the formation of complexes between NCP and the agent being tested. Alternatively, one can examine the diminution in complex formation between NCP and a receptor caused by the agent being tested.

Methods of screening for drugs or any other agents which can affect macrophage activation comprise contacting such an agent with NCP fragment and assaying for the presence of a complex between the agent and the NCP fragment. In such assays, the NCP fragment is typically labelled. After suitable incubation, free NCP fragment is separated from that present in bound form, and the amount of free or uncomplexed label is a measure of the ability of the particular agent to bind to NCP.

Another technique for drug screening provides high throughput screening for compounds having suitable binding affinity to the NCP polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with NCP fragment and washed. Bound NCP fragment is then detected by methods well known in the art. Purified NCP can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding NCP specifically compete with a test compound for binding to NCP fragments. In this manner, the antibodies can be used to detect the presence of any peptide which shares one or more antigenic determinants with NCP.

XV Identification of Molecules Which Interact with NCP

The inventive purified NCP is a research tool for identification, characterization and purification of interacting molecules. Appropriate labels are incorporated into NCP by various methods known in the art and NCP is used to capture soluble or interact with membrane-bound molecules. A preferred method involves labeling the primary amino groups in NCP with $^{125}$I Bolton-Hunter reagent (Bolton, A E and Hunter, W M (1973) Biochem J 133: 529). This reagent has been used to label various molecules without concomitant loss of biological activity (Hebert C A et al (1991) J Biol Chem 266: 18989–94; McColl S et al (1993) J Immunol 150:4550–4555). Membrane-bound molecules are incubated with the labelled NCP molecules, washed to removed unbound molecules, and the NCP complex is quantified. Data obtained using different concentrations of NCP are used to calculate values for the number, affinity, and association of NCP.

Labelled NCP fragments are also useful as a reagent for the purification of molecules with which NCP interacts, specifically including inhibitors. In one embodiment of affinity purification, NCP is covalently coupled to a chromatography column. Cells and their membranes are extracted, NCP is removed and various NCP-free subcomponents are passed over the column. Molecules bind to the column by virtue of their NCP affinity. The NCP-complex is recovered from the column, dissociated and the recovered molecule is subjected to N-terminal protein sequencing or other identification procedure. If the captured molecule has an amino acid sequence, it can be used to design degenerate oligomers for use in cloning the gene from an appropriate cDNA library.

In an alternate method, monoclonal antibodies raised against NCP fragments are screened to identify those which inhibit the binding of labelled NCP. These monoclonal antibodies are then used in affinity purification or expression cloning of associated molecules. Other soluble binding molecules are identified in a similar manner. Labelled NCP is incubated with extracts or other appropriate materials derived from lung, kidney or other tissues with activated monocytes or macrophages. After incubation, NCP complexes (which are larger than the lone NCP fragment) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XVI Use and Administration of Antibodies or Inhibitors to NCP

The antibodies and inhibitors can provide different effects when administered therapeutically. The antibodies and inhibitors are used to lessen or eliminate undue damage caused by disorders or diseases associated with upregulated NCP expression. Each of these molecules or treatments (TSTs) will be formulated in a nontoxic, inert, pharmaceutically acceptable aqueous carrier medium preferably at a pH of about 5 to 8, more preferably 6 to 8, although the pH may vary according to the different characteristics of the peptide, antibody or inhibitor being formulated and the condition to be treated. Characteristics of TSTs include solubility of the molecule, half-life, antigenicity/immunogenicity and the ability of the inhibitor to reach its target(s). These and other characteristics may aid in defining an effective carrier. Native human proteins are preferred as TSTs, but recombinant peptides as well as organic or synthetic molecules resulting from drug screens may be equally effective in particular situations.

TSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TST to be administered, and the pharmacokinetic profile of the particular TST. Additional factors which may be taken into account include disease state (eg. severity) of the patient, age, weight, gender, diet, time and frequency of administration, drug combination, reaction sensitivities, and tolerance/response to therapy. Long acting TST formulations might be administered every 3 to 4 days, every week, or once every two weeks depending on half-life and clearance rate of the particular TST.

Normal dosage amounts may vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art will employ different formulations for different TSTs. Administration to lung cells may necessitate delivery in a manner different from that to kidney or other cells.

It is contemplated that conditions associated with altered NCP expression are treatable with TSTs. These conditions, which specifically include, but are not limited to, anemia, arteriosclerosis, asthma, bronchitis, emphysema, gingivitis, inflammatory bowel disease, insulin-dependent diabetes mellitus, leukemia, multiple endocrine neoplasias, osteoarthritis, osteoporosis, pulmonary fibrosis, rheumatoid arthritis, septic shock syndromes, and systemic lupus erythematosus may be specifically diagnosed by the tests discussed above. In addition, such tests may be used to monitor treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. An antisense molecule comprising the complement of the polynucleotide sequence of SEQ ID NO:1.

2. A composition comprising an antisense molecule of claim 1 and an aqueous carrier.

3. A kit comprising a purified polynucleotide comprising the polynucleotide sequence SEQ IN NO:1 or its complement, a detectable label, and means for detecting said label.

4. A method of detecting expression of a polynucleotide comprising the polynucleotide sequence of SEQ ID NO:1 in a biological sample, said method comprising the steps of:
   a) combining the biological sample with a purified polynucleotide comprising the polynucleotide sequence of SEQ ID NO:1 or its complement;
   b) allowing hybridization to occur between nucleic acids of the biological sample and the purified polynucleotide under conditions suitable for formation of a hybridization complex between the purified polynucleotide and its complement;
   c) detecting the hybridization complex, wherein the presence of the hybridization complex is correlated with the expression of the polynucleotide comprising the polynucleotide sequence of SEQ ID NO:1 in the biological sample.

5. A method of inhibiting expression of a nucleic acid comprising the nucleic acid sequence of SEQ ID NO:1 in a cell, in vitro, said method comprising providing the polynucleotide of claim 1 to a cell expressing said nucleic acid.

6. A method of claim 5, wherein the polynucleotide is provided by co-expression in the cell.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1855 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: Adrenal
      (B) CLONE: 100877

(xi) SEQUENCE DESCRIPTION: SEQ ID NO:1:

```
AATTCGGCAC GAGGCCTGCC ACAGGTGTCT GCAATTGAAC TCCAAGGTGC AGAATGGTTT      60

GGAAAGTAGT TGTATTCCTC AGTGTGGCCC TGGGAATTGG TGCCGTTCCT ATAGATGATC     120

CTGAAGATGG AGGCAAGCAC TGGGTGGTGA TCGTGGCAGG TTCAAATGGC TGGTATAATT     180

ATAGGCACCA GGCAGACGCG TGCCATGCCT ACCAGTTCAT TCACCGCAAT GGGATTCCTG     240

CCGAACAGAT CGTTGTGATT ATGTACGATG ACATAGCTTA CTCTGAAGAC AATCCCACTC     300

CAGGAATTGT GATCAACAGG CCCAATGGCA CAGATGTCTA TCAGGGAGTC CCGAAGGACT     360

ACACTGGAGA GGATGTTACC CCACAAAATT TCCTTGTTGT GTTGAGAGGC GATGCAGAAG     420

CAGTGAAGGG TATAGGATCC CGCAAAGTCC TGAAGAGTGG TCCCCAGGAT CACGTGTTCA     480

TTTATTTCAC TGACCATGGA TCTTCTGGAA TACTGGTTTT CCCCAATGAA GATCTTCATG     540

TAAAGGACCT GATTAAGACC ACCCATTACA TTTTCAAAAA CAAAATGTAC CGAAAGATGG     600

TGTTCTACAT TGAGGCCTGT GAGTCTGGGT CCATGATGAA CCACCTGCCG GATAACATCA     660

ATGTTTATGC AACTACTGCT GCCAACCCCA GAGAGTCGTC CTACGCCTGT TACTATGATG     720

AGAAGAGGTC CACGTACCTG GGGGACTGGT ACAGCGTCAA CTGGATGGAA GACTCGGACG     780

TGGAAGATCT GACTAAAGAG ACCCTGCACA AGCAGTACCA CCTGGTAAAA TCGCACACCA     840

ACACCAGCCA CGTCATGCAG TATGGAAACA AAACAATCTC CACCATGAAA GTGATGCAGT     900

TTCAGGGTAT GAAACGCAAA GCCAGTTCTC CCGTCCCCCT ACCTCCAGTC ACACACCTTG     960

ACCTCACCCC CAGCCCTGAT GTGCCTCTCA CCATCATGAA AAGGAAACTG ATGAACACCA    1020
```

```
ATGATCTGGA GGAGTCCAGG CAGCTCACGG AGGAGATCCA GCGGTATCTG GATGCCAGGC    1080

ACCTCATCCG AGGTGAGGTG GAGCAGCTCC TGTCCGAGAG AGCCCCGCTC ACGGGGCACA    1140

GCTGCTACCC AGAGGTCCTG TTGTACTTCC GGACCCACTG CTTCAACTGG TACTCCCCCA    1200

CGTACGAGTT ATGTGTTGAG ACATTTTGTA CGTGTTGGTC AACCTTTGTG AGAAGGCGCT    1260

TCCACTTCAC AGGATATAAT TGTCCATGGC CCACGTGTGC CTTGGTCACT ACTGAAGAGC    1320

TGCCTCCTGG AAGCTTTTCC CAAGTGTGAG CGCCCCCACC GGCTGTGTTC TTGATCAAGA    1380

GACTGGAGAG GTGGAGTGAG AAGTCTCCGC TGCTCGGGCC CTCCTGGGGG ACCCCCCGCT    1440

CCAGGGCTCG CTCCAGGACC TTCTTCACAA GATGACTTGC TCGCTGTTAC CTGCTTCCCC    1500

AGTCTTTTCT GAAAAACTAC AAATTAGGGT GGGAAAAGCT CTGTATTGAG AAGGGTCATA    1560

TTTGCTTTCT AGGAGGTTTG TTGTTTTGCC TGTTAGTTTT GAGGAGCAGG AAGCTCATGG    1620

GGGCTTCTGT AGCCCCTCTC CAAAGGAGTC TTTATTCTGA GAATTTGAAG CTGAAACCTC    1680

TTTAAATCTT CAGAATGATT TTATTGAAGA GGGCCGCAAG CCCCAAATGG AAAACTGTTT    1740

TTAGAAAATA TGATGATTTT TGATTGCTTT TGTATTTAAT TCTGCAGGTG TTCAAGTCTT    1800

AAAAAATAAA GATTTATAAC AGAACCCCAA AAAAAAAAAA AAAAAAAAA AAAAA          1855
```

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Trp Lys Val Val Phe Leu Ser Val Ala Leu Gly Ile Gly
  1               5                  10                  15

Ala Val Pro Ile Asp Asp Pro Glu Asp Gly Lys His Trp Val Val
                 20                  25                  30

Ile Val Ala Gly Ser Asn Gly Trp Tyr Asn Tyr Arg His Gln Ala Asp
             35                  40                  45

Ala Cys His Ala Tyr Gln Phe Ile His Arg Asn Gly Ile Pro Ala Glu
         50                  55                  60

Gln Ile Val Val Ile Met Tyr Asp Asp Ile Ala Tyr Ser Glu Asp Asn
 65                  70                  75                  80

Pro Thr Pro Gly Ile Val Ile Asn Arg Pro Asn Gly Thr Asp Val Tyr
                 85                  90                  95

Gln Gly Val Pro Lys Asp Tyr Thr Gly Glu Asp Val Thr Pro Gln Asn
                100                 105                 110

Phe Leu Val Val Leu Arg Gly Asp Ala Glu Ala Val Lys Gly Ile Gly
            115                 120                 125

Ser Arg Lys Val Leu Lys Ser Gly Pro Gln Asp His Val Phe Ile Tyr
        130                 135                 140

Phe Thr Asp His Gly Ser Ser Gly Ile Leu Val Phe Pro Asn Glu Asp
145                 150                 155                 160

Leu His Val Lys Asp Leu Ile Lys Thr Thr His Tyr Ile Phe Lys Asn
                165                 170                 175

Lys Met Tyr Arg Lys Met Val Phe Tyr Ile Glu Ala Cys Glu Ser Gly
                180                 185                 190

Ser Met Met Asn His Leu Pro Asp Asn Ile Asn Val Tyr Ala Thr Thr
            195                 200                 205
```

```
Ala Ala Asn Pro Arg Glu Ser Ser Tyr Ala Cys Tyr Tyr Asp Glu Lys
    210                 215                 220

Arg Ser Thr Tyr Leu Gly Asp Trp Tyr Ser Val Asn Trp Met Glu Asp
225                 230                 235                 240

Ser Asp Val Glu Asp Leu Thr Lys Glu Thr Leu His Lys Gln Tyr His
                245                 250                 255

Leu Val Lys Ser His Thr Asn Thr Ser His Val Met Gln Tyr Gly Asn
            260                 265                 270

Lys Thr Ile Ser Thr Met Lys Val Met Gln Phe Gln Gly Met Lys Arg
        275                 280                 285

Lys Ala Ser Ser Pro Val Pro Leu Pro Pro Val Thr His Leu Asp Leu
290                 295                 300

Thr Pro Ser Pro Asp Val Pro Leu Thr Ile Met Lys Arg Lys Leu Met
305                 310                 315                 320

Asn Thr Asn Asp Leu Glu Glu Ser Arg Gln Leu Thr Glu Glu Ile Gln
                325                 330                 335

Arg Tyr Leu Asp Ala Arg His Leu Ile Arg Gly Glu Val Glu Gln Leu
            340                 345                 350

Leu Ser Glu Arg Ala Pro Leu Thr Gly His Ser Cys Tyr Pro Glu Val
        355                 360                 365

Leu Leu Tyr Phe Arg Thr His Cys Phe Asn Trp Tyr Ser Pro Thr Tyr
        370                 375                 380

Glu Leu Cys Val Glu Thr Phe Cys Thr Cys Trp Ser Thr Phe Val Arg
385                 390                 395                 400

Arg Arg Phe His Phe Thr Gly Tyr Asn Cys Pro Trp Pro Thr Cys Ala
                405                 410                 415

Leu Val Thr Thr Glu Glu Leu Pro Pro Gly Ser Phe Ser Gln Val
                420                 425                 430

(2) INFORMATION FOR SEQ ID NO:3:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (E) HAPLOTYPE: U937

(vii) IMMEDIATE SOURCE:
          (A) LIBRARY: 001098

(xi) SEQUENCE DESCRIPTION: SEQ ID NO:3:

ATTTGCTTTC TAGGAGGTTT GTTGTTTTGC CTGTTAGTTT TGAGGAGCAG GAAGCTCATG    60

GGGGCTTCTG TAGCCCCTCT CAAAAGGAGT CTTTATTCTG AGAATTTGAA GCTGAAACCT   120

CTTTAATCTT CAGAATGATT TTATTGAAGA GGGCCGCAAG CCCCAAATGG AAAACTGTTT   180

TTAGAAAATA TGATGATTTT TGATTGCTTT TGTATTTAAT TCTGCAGGTG TTCAAGTCTT   240

AAAAAATAAA GATTTATAAC AGAACCC                                       267

(2) INFORMATION FOR SEQ ID NO:4:

(i) SEQUENCE CHARACTERISTICS:
        (A) LENGTH: 195 base pairs
        (B) TYPE: nucleic acid
        (C) STRANDEDNESS: single
        (D) TOPOLOGY: linear
```

(ii) MOLECULE TYPE: cDNA (vii) IMMEDIATE SOURCE:
    (A) LIBRARY: Huvec
    (B) CLONE: 066931

(xi) SEQUENCE DESCRIPTION: SEQ ID NO:4:

```
ACGGAGGAGA TCAGCGGCAT CTGGATGCAG GCACCTCATT GAGAAGTCAG TGCGTAAGAT    60

CGCTCATTCT GGCAGCGTCC GAGGCTGAGG TGGAGCAGCT CCTGTCCGAG AGAGCCCCGC   120

TCACGGGGAC AGCTCTACCC AGAGGCCCTG CTGCACTTCG ACCCACTCT TAACTGCACT    180

CCCCCACGTA CGAGT                                                    195
```

(2) INFORMATION FOR SEQ ID NO:5:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: THP-1
        (B) CLONE: 075848

(xi) SEQUENCE DESCRIPTION: SEQ ID NO:5:

```
GAAGAGGT CCACGTACCT GGGGGACTGG TACAGCNTCA ACTGGATGGA AGACTCGGAC      60

GTGGAAGATC TGACTAAAGA GACCCTGCAC AAGCAGTACC ACCTGGTAAA ATCGCACACC   120

AACACCAGCC ACGTCATGCA GTATGGAAAC AAAAC                              155
```

(2) INFORMATION FOR SEQ ID NO:6:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Rheumatoid Synovium
        (B) CLONE: 077015

(xi) SEQUENCE DESCRIPTION: SEQ ID NO:6:

```
GAAACGCAAA GCCAGTTCTC CCGTCCCCCT ACCTCCAGTC ACACACCTTG ACCTCACCCC    60

CAGCCCTGAT GTGCCTCTCA CCATCATGAA AAGGAAACTG ATGAACACCA ATGATCTGGA   120

GGAGTCCAGG CAGCTCACGG NGGAGATCCA GCGGCATCTG GATGNCAGGC ACCTCATTGA   180

GAAGTCAGTG CGTAAGATCG TCTCCTTGCT GGNAGCGTCC GAGGCTGAGG TGGAGCAGCT   240

CCTTA                                                              245
```

(2) INFORMATION FOR SEQ ID NO:7:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Rheumatoid Synovium
        (B) CLONE: 077424

(xi) SEQUENCE DESCRIPTION: SEQ ID NO:7:

GATGTGCTCT ACCATCATGA AAAGGAAACT ATGAACACCA ATATCTGGAG GAGTCCAGGC        60

AGCTCACGGA GGAGATCCAG CGGCATCTGG ATGCCAGGCA CCTCATTGAG AAGTCAGTGC       120

GTAAATCGTT CCTTGCTGGC AGCGTCCGAG GCTGAGGTGG AGCAGCTCCT TCCGAGAGAG       180

CCCCG                                                                  185

(2) INFORMATION FOR SEQ ID NO:8

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Rheumatoid Synovium
        (B) CLONE: 077645

(xi) SEQUENCE DESCRIPTION: SEQ ID NO:8:

AGAGACTGGA GAGGTGGAGT GAGAAGTCTC CGCTGCTCGG GCCTCCTGGG GAGCCCCCGC        60

TCCAGGGCTC GCTCCAGGAC CTTCTTCACA AGATGACTTN NTCGCTGTTA CCTGCTTCCC       120

CAGTCTTTTC TGNAAAACTA CAAATTAGGG TGGGAAAAGC TCTGTATTGA GAAGGGTCAT       180

ATTTGCTTTC TAGGAGGTTT GTTGTTTTGC CTGTAAGTTT TGAGGAGCAG GA              232

(2) INFORMATION FOR SEQ ID NO:9:

(i) SEQUENCE CHARACTERISTICS:
        (A) LENGTH: 253 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Rheumatoid Synovium
        (B) CLONE: 077651

(xi) SEQUENCE DESCRIPTION: SEQ ID NO:9:

TGCACAAGCA GTACCACCTG GTAAAATCGC ACACCAACAC CAGCCACGTC ATGCAGTATG        60

GAAACAAAAC AATCTCCACC ATGAAAGTNA TGCAGTTTCA GGGTATGAAA CGCAAAGCCA       120

GTTCTCCCGT CCCCCTACCT TCAGTCACAC ACCTTGACCT CACCCCCAGC CCTGATGTGC       180

CTCTNACCAT CATGAAAAGG GTAACTGNTG AACACCAATN ATCTTGAGGA GTCCAGGNAG       240

CTTTACGGTG GTT                                                         253

2) INFORMATION FOR SEQ ID NO:10:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Rheumatoid Synovium
        (B) CLONE: 078547

(xi) SEQUENCE DESCRIPTION: SEQ ID NO:10:

```
ACTGGATGGA AGACTCGGAC GTGGAAGATC TGACTAAAGA GACCCTGCAC AAGCAGTACC    60

ACCTGGTAAA ATCGCACACC AACACCAGCC ACGTCATGCA GTATGGAAAC AAAACANTCT   120

CCACCATGAA AGTNATGCAG TTTCAGGGTA TGAAACGCAA AGCCAGTTCT CCCGTCCCCC   180

TACCTCCAGT CACACACCTT TGACCCTCAC CCCCAGNCCT GATGTGCCTC TAACCATCAT   240

GNAAAGGAAA CTGGATGGAC ACCAATGATC TGGGAGGAGT CCAGGGAAGG NTCACGGAGG   300

GNGATCCCAG CGGGNATCTG GGATTCCCAN N                                 331

(2) INFORMATION FOR SEQ ID NO:11:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Bone Marrow
        (B) CLONE: 104286

(xi) SEQUENCE DESCRIPTION: SEQ ID NO:11:

GTTTATGCAA CTNCTGCTGC CAACCCCAGA GAGTCGTCCT ACGCCTGTNA CTATGATGAG    60

AAGAGGTCCA CGTACCTGGG GGACTGGTAC AGCGTCAACT GGATGGAAGA CTCGGACGTG   120

GAAGATCTGA CTAAAGAGAC CCTGCACAAG CAGTACCACC TGGTAAAATC GCACACCAAC   180

ACCAGCCACG TCATGCAGTA TGGAAACAAA ACANTCTCC                          219

(2) INFORMATION FOR SEQ ID NO:12:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Kidney
        (B) CLONE: 115565

(xi) SEQUENCE DESCRIPTION: SEQ ID NO:12:

CACTACTGA AGAGCTGCCT CCTGGAAGCT TTTCCAAGTN TGAGCGCCCC ACCGACTGTT     60

TGCTGATCAN AGACTGGAGA GGTGGAGTGA GAAGTCTCCG CTGCTCGGGC CCTCCTGGGG   120

AGCCCCCGCT CCAGGGCTCG CTCCAGGACC TTNTTCACAA GATGACTTGC TCGCTGTTAC   180

CNGCTTCCCC AGTCTTTTNT GAAAAACTAC AAATTAGGGT GGGAAAAGCT CTGTATTGAG   240

AAGGGTCATA TTTNCTTTCT AGGAGGTTTT T                                  271

(2) INFORMATION FOR SEQ ID NO:13:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Lung
        (B) CLONE: 125569

(xi) SEQUENCE DESCRIPTION: SEQ ID NO:13:
```

```
GTTCTACATT GANGCCTGTG AGTCTGGGTC CATGATGAAC CACCTNCCGG ATAACATCAA        60

TGTTTATGCA ACTACTGCTG CCAACCCCAG AGAGTCGTCC TACGCCTGTT ACTATGATGA       120

GAAGAGGNCC ACGTACCTGG GGGACTNGTA CAAAGTNAAA NTNGATGGAA GAATTCAGAC       180

GAGGAAGATC TNNCTAAAAN AGAACCTTAA CAAANCANTA ACNCCTAAG                   229
```

(2) INFORMATION FOR SEQ ID NO:14:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Lung
        (B) CLONE: 125830

(xi) SEQUENCE DESCRIPTION: SEQ ID NO:14:

```
CCAGAGNCCT GCNGCACTTC CGGACCCACT GCTTCAACTG GCACTCCCCC ACGTACGAGT        60

ATGCNTTGAG ACATTTGTAC GTGCTGGTCA ACCTTTGTNA GAAGCCGTAT CCACTTCACA       120

GGATAAAATT GTCCATGGAC CACGTGTGCC TTGGTCACTA CTGANGAGCT GCCTCCTGGA       180

AGCTTTTCCA AGTNTGAGCG CCCCACC                                           207
```

(2) INFORMATION FOR SEQ ID NO:15:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Kidney
        (B) CLONE: 158868

(xi) SEQUENCE DESCRIPTION: SEQ ID NO:15:

```
ATGAACCACC TGCCGGATAA CATCAATGTT TATGCAACTA CTGCTGCCAA CCCCAGAGAG        60

TCGTCCTACG CCTGTAACTA TGATGAGAAG AGGTCCACGT ACCTGGGGGA CTGGTACAGC       120

GTCAACTGGA TGGAAGACTC GGACGTGGAA GATCTGACTA AGAGACCCT GCACAAGCAG        180

TACCACCTGG TAAAATCGCA CACCAACACC AGCCACGTTG                             220
```

(2) INFORMATION FOR SEQ ID NO:16:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Adenoid
        (B) CLONE: 162199

(xi) SEQUENCE DESCRIPTION: SEQ ID NO:16:

```
GTACCACCTG GTAAAATCGC ACACCAACAC CAGCCACGTC ATGCAGTATG GAAACAAAAC        60

AATCTCCACC ATGAAAGTGA TGCAGTTTCA GGGTATGAAA CGCAAAGCCA GTTCTCCCGT       120
```

```
CCCCCTACCT CCAGTCACAC ACCTTGACCT CACCCCCAGC CCTGATGTGC CTCTCACCAT    180

CATGAAAAGG AAACTGATGA ACACCAATGA TCTGGAGGAG TCCAGGCAGC TCACGGGAGG    240

AGATCCAGCG GCAT                                                     254
```

(2) INFORMATION FOR SEQ ID NO:17:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Bone Marrow
        (B) CLONE: 172499

(xi) SEQUENCE DESCRIPTION: SEQ ID NO:17:

```
AAATTGTCCA TGGACCACGT GTGCCTTGGT CACTACTGAA GAGCTGCCTC CTGGAAGCTT     60

TTCCAAGTGT GAGCGCCCCA CCGACTGTNT GCTGATCAGA GACTGGAGAG GTGGAGTGAG    120

AAGTCTCCGC TGCTCGGGCC CTCCTGGGGA GCCCCCGCTC CAGGNCTCGC TCCAGGACCT    180

TCTTCACAAG ATGACTTGCT CGCTGTTACC TGCTTCCG                            218
```

(2) INFORMATION FOR SEQ ID NO:18:

(i) SEQUENCE CHARACTERISTICS:
        (A) LENGTH: 199 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Bone Marrow
        (B) CLONE: 174690

(xi) SEQUENCE DESCRIPTION: SEQ ID NO:18:

```
GNGACTGGTA CAGCNTCAAC TGGNTGGAAG NCTNGGACGT GGAAGATCTG ACTAANGAGA     60

CCCTGCACAA GCAGTACCAC CTGGTAAAAT CGNACANCAA NACCAGCCAC GTCATGCAGT    120

ATGGGACAAN NCAATCTCCA CCATGAAAGT GATGCAGTTT CAGGGTATGA AACGCAGAGC    180

CATNTTCTCC CGTTCNACT                                                 199
```

(2) INFORMATION FOR SEQ ID NO:19:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Placenta
        (B) CLONE: 180594

(xi) SEQUENCE DESCRIPTION: SEQ ID NO:19:

```
GGCCCGGGCA GCGGAGACTT CTCACTCCAC CTCTCCAGTC TCTGATCAGC AC             52
```

(2) INFORMATION FOR SEQ ID NO:20:

(i) SEQUENCE CHARACTERISTICS:
        (A) LENGTH: 51 base pairs (B) TYPE: nucleic acid
            (C) STRANDEDNESS: single
            (D) TOPOLOGY: linear (ii) MOLECULE TYPE: cDNA (vii) IMMEDIATE SOURCE:
            (A) LIBRARY: Placenta
            (B) CLONE: 180935

(xi) SEQUENCE DESCRIPTION: SEQ ID NO:20:

GGCCGGGCAG CGGAGACTTC TCACTCCACC TCTCCAGTCT CTGATCAGCA C         51

(2) INFORMATION FOR SEQ ID NO:21:

(i) SEQUENCE CHARACTERISTICS:
            (A) LENGTH: 234 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (A) LIBRARY: Rheumatoid Synovium
            (B) CLONE: 190299

(xi) SEQUENCE DESCRIPTION: SEQ ID NO:21:

AGCAGCTCCT GTCCGANAGA GCCCCGCTCA CGGGGCACAG CTGCTACCCA GAGGCCCTGC      60

TGCACTTCCG GACCCACTGC TTCAACTGGC ACTCCCCCAC GTACGAGTAT GCNTTGAGAC     120

ATTTGTACGT GCTGGTCAAC CTTTGTNAGA AGCCGTATCC GCTTCANAGG ATAAAATTGT     180

CCATGGACCA CGTGTGCCTT GGTCACTACT GAAGAGCTGC CTCCTGGAAG CTTT          234

(2) INFORMATION FOR SEQ ID NO:22:

(i) SEQUENCE CHARACTERISTICS:
            (A) LENGTH: 206 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (A) LIBRARY: Kidney
            (B) CLONE: 195541

(xi) SEQUENCE DESCRIPTION: SEQ ID NO:22:

CTGGTTTTNC CCAATGAAGA TCTTCATGTA AAGGACCTGA NTGAGACCAT CCATTACATG      60

TACAAACACA AAATGTACCG AAAGATGGTG TTCTACATTN AGGCCTGTNA GTCTGGGTCC     120

ATGTTGANCC ACCTGCCGGN NANCATCAAN GTTNNTGCAA CTACTGNTNC CAACCCCTGA     180

GAGTNGTCCG ANGNCTGTNA CTATGT                                          206

(2) INFORMATION FOR SEQ ID NO:23:

(i) SEQUENCE CHARACTERISTICS:
            (A) LENGTH: 181 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (A) LIBRARY: Kidney
            (B) CLONE: 197617

(xi) SEQUENCE DESCRIPTION: SEQ ID NO:23:

-continued

```
CTAAAGAGAC CCTGCACAAG CAGTACCACC TGGTAAAATC GCACACCAAC ACCAGCCACG        60

TCATGCAGTA TGGAAACAAA ACAATCTNCA CCATGAAAGT NATGCAGTTT CAGGGTATGA       120

AACGCAAAGC CAGTTCTCCC GTCCCCCTAC CTCCAGTCAC ACACCTTGAC CTCACCCCCN       180

T                                                                      181

(2) INFORMATION FOR SEQ ID NO:24:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: Small Intestine
        (B) CLONE: 238970

(xi) SEQUENCE DESCRIPTION: SEQ ID NO:24:

ACTACTGAAG AGCTGCCTCC TGGAAGCTTT TCCAAGTGTG AGCGCCCCAC CGACTGTTTG        60

CTGATCAGAG ACTGGAGAGG TNGAGTNAGA AGTCTCCGCT GCTCGNGCCC TCCTGGGGAG       120

CCCCCGCTCC AGGGCTCGCT CCAGGACCTT NTTCACAAGA TGACTTGCTC GCTGTTACCT       180

GCTTCCCCAG TCTTTTCTGA AAAACTACAA AA                                     212
```